(12) United States Patent
Mewshaw et al.

(10) Patent No.: US 6,610,712 B2
(45) Date of Patent: Aug. 26, 2003

(54) ARYLOXY PIPERIDINYL DERIVATIVES FOR THE TREATMENT OF DEPRESSION

(75) Inventors: Richard E. Mewshaw, King of Prussia, PA (US); Dahui Zhou, East Brunswick, NJ (US); Ping Zhou, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/000,642

(22) Filed: Nov. 15, 2001

(65) Prior Publication Data

US 2002/0091141 A1 Jul. 11, 2002

Related U.S. Application Data

(60) Provisional application No. 60/252,140, filed on Nov. 16, 2000.

(51) Int. Cl.$^7$ .................... C07D 401/04; A61K 31/443
(52) U.S. Cl. ................. 514/338; 514/339; 514/323; 546/277.4; 546/201
(58) Field of Search ................. 546/277.4, 201; 514/323, 338, 339

(56) References Cited

U.S. PATENT DOCUMENTS

| 5,114,949 | A | | 5/1992 | Gueremy et al. |
| 6,476,051 | B2 | * | 11/2002 | Mattson et al. ............. 548/159 |
| 2002/0147344 | A1 | * | 10/2002 | Scantacana et al. ........ 546/201 |

FOREIGN PATENT DOCUMENTS

| EP | 169 148 A1 | 1/1986 |
| EP | 0 714 894 A1 | 6/1996 |
| EP | 0 722 941 A2 | 7/1996 |
| WO | WO 99/05140 A1 | 2/1999 |
| WO | WO 99/55672 A2 | 11/1999 |
| WO | WO 99/55697 A1 | 11/1999 |
| WO | WO 01/43740 A1 | 6/2001 |
| WO | WO 01/49680 A1 | 7/2001 |

OTHER PUBLICATIONS

CA 136:369609, Fonquerna et al. "Praeparation of indolylpiperidines as antihistaminnic and antiallergic agents", 2002.*
CA 129:148993, Audia et al. 1998.*
CA 125:142553, Audia at al. 1996.*
Malleron et al., New Indole Derivatives as Potent and Selective Serotonin Uptake Inhibitors., J. Med. Chem. 1993, 36, 1194–1202.

* cited by examiner

*Primary Examiner*—Jane Fan
(74) *Attorney, Agent, or Firm*—Joseph M. Mazzarese; Kimberly R. Hild

(57) ABSTRACT

This invention provides compounds useful in treating serotonin-related central nervous system disorders, including anxiety, generalized anxiety disorder, panic disorder, obsessive-compulsive disorder, sleep disorders, sexual dysfunction, alcohol and drug addiction, Alzheimer's disease, Parkinson's disease, obesity and migraine, the compounds having the general formula:

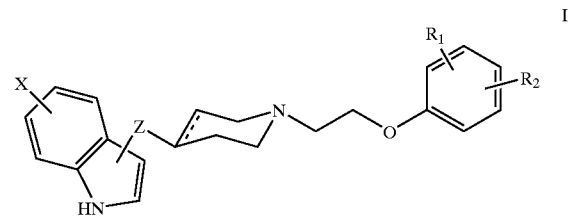

wherein: $R_1$ and $R_2$ may each be H or an alkyl or alkoxy group; or $R_1$ and $R_2$ may be concatenated to form a bicyclic ring system with the phenyl ring to which they are bound; X is selected from hydrogen, halogen, cyano, $C_1$–$C_6$ alkoxy; Z is $(CH_2)n$ or carbonyl; n is 0, 1 or 2; the dashed line indicates an optional double bond; or a pharmaceutically acceptable salt thereof.

15 Claims, No Drawings

ARYLOXY PIPERIDINYL DERIVATIVES FOR THE TREATMENT OF DEPRESSION

This application claims priority from copending provisional application(s) serial No. 60/252,140 filed on Nov. 16, 2000, the entire disclosure of which is hereby incorporated by reference.

This invention relates to new aryloxy indole derivatives as pharmaceuticals which are useful for the treatment in mammals of diseases affected by disorders of the serotonin-affected neurological systems, such as depression, anxiety, panic disorder, obsessive-compulsive disorder, sleep disorders, sexual dysfunction, alcohol and drug, addiction, Alzheimer's disease, Parkinson's disease, obesity and migraine, as well as methods of enhancing cognition.

BACKGROUND OF THE INVENTION

EP 0714894 A1 discloses the preparation of compounds of formula II as new $5\text{-}HT_{1f}$ agonist for the treatment of migraine headaches. EP 429341 A2 claims compounds of formula III as having serotonin transporter activity. A recent publication by Malleron et al. was also reported based around formula I [J. Med. Chem. 36, 1194 (1993)]. EP 722941 A2 discloses compounds having effects on serotonin-related systems of formula IV.

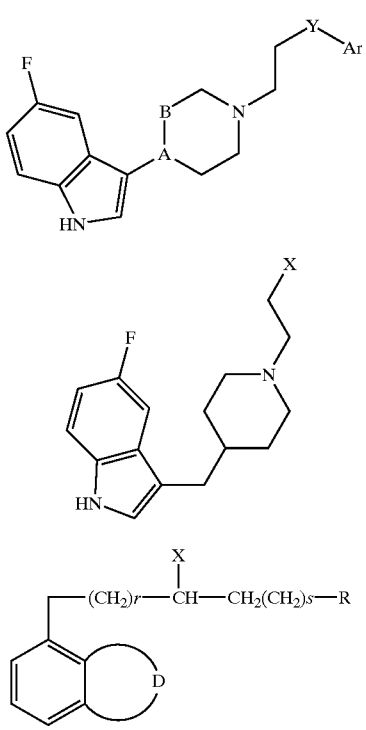

Pharmaceuticals which enhance serotonergic neurotransmission are of useful benefit for the treatment of many psychiatric disorders, including depression and anxiety. The first generation of non-selective serotonin-affecting drugs operated through a variety of physiological functions which endowed them with several side effect liabilities. The more currently prescribed drugs, the selective serotonin (5-HT) reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism per se cannot account for their therapeutic activity. It is speculated that this two week induction which occurs before a full antidepressant effect is observed, is due to the involvement of the $5\text{-}HT_{1A}$ autoreceptors which suppress the firing activity of 5-HT neuron, causing a dampening of the therapeutic effect. Studies suggest that after several weeks of SSRI administration, a desensitization of the 5-HT autoreceptors occurs allowing a full antidepressant effect in most patients. Recent studies by Artigas et al. (Trends Neurosci., 1996, 19, 378–383) suggest a combination of $5\text{-}HT_{1A}$ activity and inhibition of 5-HT uptake within a single molecular entity can achieve a more robust and fast-acting antidepressant effect.

The present invention relates to a new class of molecules which have the ability to act at the $5\text{-}HT_{1A}$ autoreceptors and concomitantly with the 5-HT transporter. Such compounds are therefore potentially useful for the treatment of depression as well as other serotonin disorders.

SUMMARY OF INVENTION

The compounds of this invention are aryloxy piperidinyl indoles represented by Formula I:

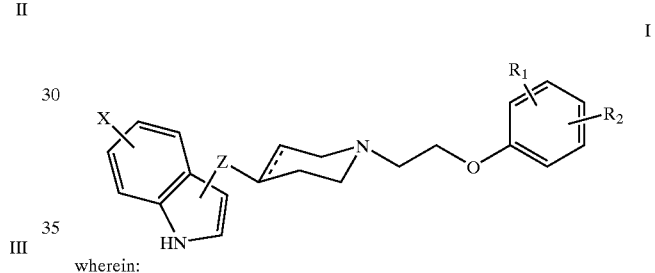

wherein:

$R_1$ and $R_2$ may each be hydrogen or an alkyl of from 1 to 6 carbon atoms or an alkoxy group of from 1 to 6 carbon atoms; or $R_1$ and $R_2$ may be concatenated to comprise another ring system wherein the ring contains a total of 5–7 ring members;

X is selected from hydrogen, halogen, cyano, $C_1$–$C_6$ alkoxy;

Z is $(CH_2)n$ or carbonyl;

n is 0, 1 or 2;

the dashed line indicates an optional double bond; or a pharmaceutically acceptable salt thereof.

Ring systems formed by the concatenation of $R_1$ and $R_2$ are understood to contain the carbon or oxygen atoms of the $R_1$ and $R_2$ groups and can being saturated or unsaturated, including fused alkyl, pyran, or dioxan ring systems. With the phenyl ring to which they are bound, the concatenated rings can form the moieties:

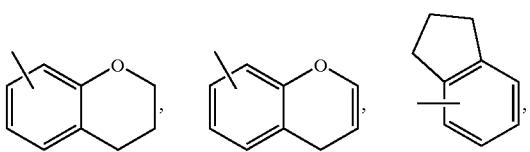

-continued

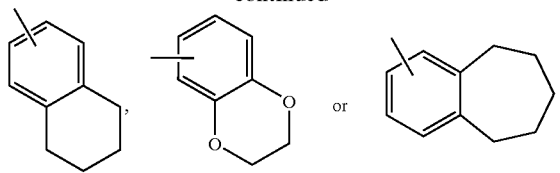 or 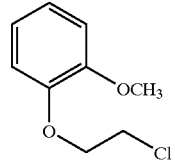

One group of compounds of this invention comprises compounds of the formula:

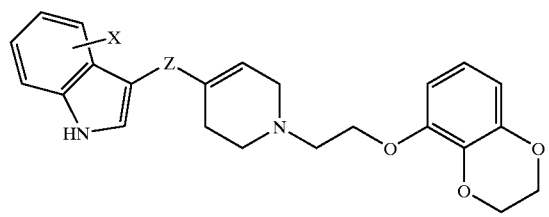

wherein X is selected from H, halogen, cyano, $C_1$–$C_6$ alkoxy; Z is $(CH_2)n$ or carbonyl;
and n is 0, 1 or 2; or a pharmaceutically acceptable salt thereof.

Another group of compounds of this invention comprises those of the formula:

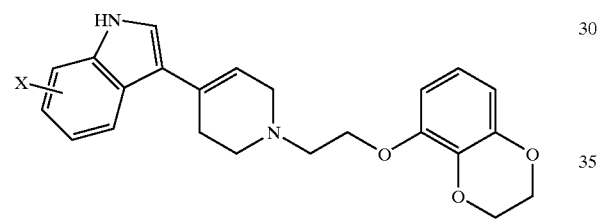

wherein X is H, halogen, cyano, $C_1$–$C_6$ alkoxy, or a pharmaceutically acceptable salt thereof.

A further group of compounds of this invention, and pharmaceutically acceptable salts thereof, are represented by the formula:

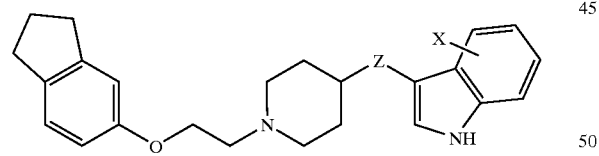

wherein X and Z are as defined above.

The compounds of this Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of Formula I are generally prepared by the overall sequence indicated in Scheme 1 and 2 as follows:

Scheme 1

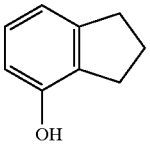

1

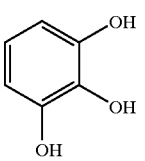

2

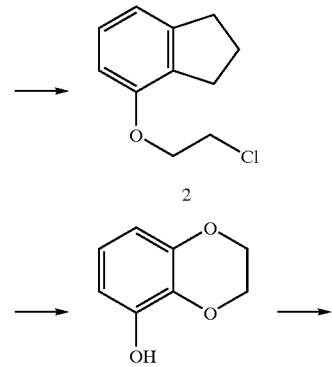

Scheme 2

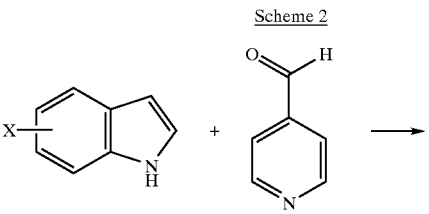

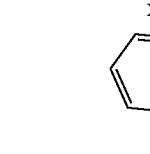

5

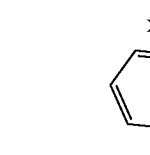

6

7

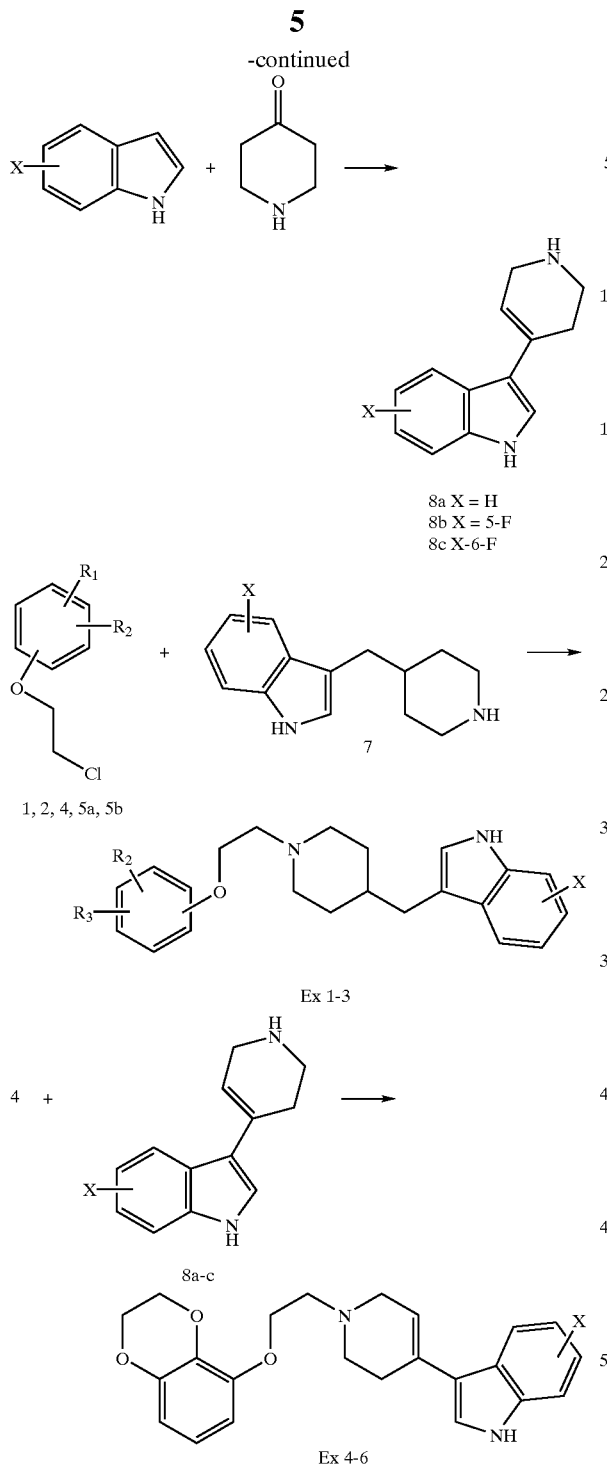

The following examples for preparation of intermediates and invention compounds are included for illustrative purposes and are not to be construed as limiting to this disclosure in any way. Those skilled in the art of organic synthesis may be aware of still other synthetic routes to the invention compounds. The reagents and intermediates used herein are either commercially available or prepared according to standard literature procedures.

Intermediate 1

1-(2-Chloroethoxy)-2-methoxybenzene.

To a solution of 2-methoxyphenol (14.4 g, 116 mmol) in 2-butanone (200 mL) was added bromochloroethane (69.0 g, 480 mmol) followed by the addition of potassium carbonate (40.0 g, 280 mmol). The reaction mixture was mechanically stirred and heated to reflux for 24 h, then cooled to room temperature. The solids were filtered off and the solvent was removed under vacuum. The residue was dissolved in diethyl ether and washed with 10% of NaOH, dried over anhydrous magnesium sulfate, filtered and concentrated. Purification by silica gel column chromatography (25% EtOAc/hexane) afforded 7.55 g (35%) of a solid: mp 36–38°C. (Lit.[2] 41–43° C,); $^1$H NMR (DMSO, 400 MHz), 3.75 (s, 3H), 3.91 (dd, 2H), 4.20 (dd, 2H), 6.86–6.99 (m, 4H); MS (EI) m/z 186 (M$^+$).

Intermediate 2

5-(2-Chloroethoxy)-indane.

Replacing 2-methoxyphenol with commercially available 5-hydroxyindane and using the above procedure afforded the title compound in 43% yield as a white solid: mp 45–46° C.

Elemental Analysis Calcd for $C_{11}H_{13}OCl$ Theory: C, 67.18; H, 6.66 Found: C, 67.03; H, 6.57

Intermediate 3

5-Hydroxy-(2,3)-dihydrobenzo[1,4]dioxan

Pyrogallol (5 g, 0.04 mmol) was dissolved in 2-butanone (600 mL) to which potassium carbonate (1.82 g, 0.013 mol) was added. The mixture was stirred at reflux while 1,2-dibromoethane (2.48 g, 1.14 mL, 0.013 mol) was slowly added drop wise. The reaction was allowed to stir overnight and then cooled to room temperature. The mixture was poured into water (100 mL) and extracted with methylene chloride (200 mL). The organic layer was dried over anhydrous sodium sulfate, filtered, and the solvent removed under vacuum. Chromatography (5% methanol-methylene chloride) afforded 2.74 g (45%) of a clear oil.

Intermediate 4

5-(2-Chloroethoxy)-(2,3)-dihydrobenzo[1,4]dioxan

To solution of 5-hydroxy benzodioxan (1 g, 6.5 mmol) and 2-chloroethanol (0.79 g, 9.9 mmol), triphenylphosphine (2.6 g, 9.9 mmol) in THF (50 mL) was slowly added diisopropylazidodicarbimide (DIAD) (2.0 g, 9.8 mmol). After 2 h, another 1.5 eq of triphenylphosphine, DIAD, and 2-chloroethanol was added and the reaction stirred for another 2 h. The reaction mixture was poured into water (100 mL), and extracted with methylene chloride (100 mL). The organic layer was separated and dried over anhydrous magnesium sulfate, filtered, and the solvent removed under vacuum. Chromatography (ethyl acetate-hexane: 1:4) afforded 1.7 g (76%) or a white solid: mp 70.5–72.5° C.

Elemental Analysis for $C_{10}H_{11}ClO_3$ Theory: C, 55.96; H, 5.17 Found: C, 55.57; H, 5.20

Intermediate 5

(5-Fluoro-1H-indol-3-yl)-pyridin-4-yl-methanol

To a stirred solution of 5-fluoroindole (3.10 g, 23.0 mmol) in methanol (10.0 mL) was added 4-pyridinecarboxaldehyde (2.20 mL, 23.0 mmol), followed by addition of NaOH (2.5 mL, 50%) at 0° C. After stirring for 1 h at 0° C., the reaction Mixture was warmed to room temperature and stirred for 3 h, followed by the addition of water (10.0 mL). The precipitate was collected by filtration and dried under vacuum to afford 5.2 g (93%) of a light yellow solid: mp 171–173° C.; $^1$H NMR (DMSO, 400 MHz), 5.85 (d, 1H), 5.93 (d, 1H), 6.86–7.34 (m, 4H), 7.43 (dd, 2H), 8.48 (dd, 2H), 11.09 (br s, 1H); MS (EI) m/z 242 (M$^+$); HRMS calcd for $C_{14}H_{12}FN_2O$ [M+H] 243.09337, found 243.09576.

Intermediate 6

5-Fluoro-3-[(4-pyridinyl)methyl]-1H-indole

To a suspension of (5-fluoro-1H-indol-3-yl)-pyridin-4-yl-methanol (0.799 g, 3.3 mmol) in methylene chloride (13 mL) was added triethylsilane (0.60 mL, 3.7 mmol) followed by trifluoroacetic acid (2.85 mL, 37 mmol) at room temperature. After addition of trifluoroacetic acid, a clear black solution was obtained. The reaction mixture was stirred overnight and the solvent and excess trifluoroacetic acid was removed on a rotary evaporator. To the residue was added saturated $Na_2CO_3$ to adjust the pH>9. The aqueous layer was extracted with methylene chloride and the combined organic extracts was washed with water, brine, dried over anhydrous sodium sulfate, filtered, and concentrated. The crude product was purified by silica gel column chromatography (methylene chloride to methylene chloride/ethyl acetate to ethyl acetate, 100% to 50% to 100%) to give 0.56 g (75%) of a solid: mp 141–142° C. [(mp 149° C.; previously reported in J. Med. Chem. 36, 1194 (1993)].

Intermediate 7

5-Fluoro-3-[(4-piperidinly)methyl]-1H-indole

This compound was prepared in 88% yield following the reported procedure (Malleron et al., J. Med. Chem. 1993, 36,1194).

Intermediate 8a–c (9c) 6-Fluoro-3-[1,2,3,6-tetrahydro-pyridin-4-yl]-1H-indole

A solution of 6-fluoroindole (2 g, 15 mmol) and 4-piperidone (3 g, 19.6 mmol) in 2 N solution of KOH in MeOH (60 mL) was stirred at reflux for 72 h. The mixture was concentrated to ¼ volume, diluted with H$_2$0 and filtered affording 2.5 g (77%) as a pale yellow solid: mp 202–204° C.; MS (APCI) m/z 217 [M+H]$^+$.

(9a) 3-[1,2,3,6-Tetrahydro-pyridin-4-yl]-1H-indole

Replacing 6-fluoroindole with indole in the above procedure afforded the title compound % as a pale yellow solid.

(9b) 5-Fluoro-3-[1,2,3,6-tetrahydro-pyridin-4-yl]-1H-indole

Replacing 6-fluoroindole with 5-fluoroindole in the above procedure afforded the title compound % as a yellow solid.

EXAMPLE 1

5-Fluoro-3-{1-[2-(2-methoxyphenoxy)ethyl]-piperidin-4-ylmethyl}-1H-indole.

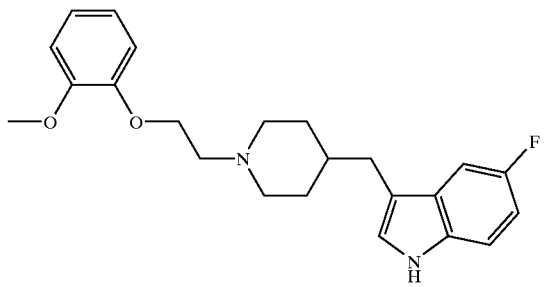

To a solution of 5-fluoro-3-[(4-piperidinyl)methyl]-1H-indole (0.60 g, 2.59 mmol) [prepared according to Malleron et al. J. Med. Chem. 36, 1194 (1993)] in DMSO (20 mL) was added 1-(2-chloroethoxy)-2-methoxybenzene (0.48 g, 2.59 mmol) followed by addition sodium carbonate (0.55 g, 5.17 mmol) at room temperature. The reaction mixture was heated to 100° C. and stirred for 5 h. After cooling to room temperature, the reaction mixture was stirred overnight, and quenched with water, diluted with methylene chloride. The two layers were separated and the aqueous was extracted with methylene chloride. The combined organic extracts were washed with water, dried over anhydrous sodium sulfate, filtered and concentrated. Purification by silica gel column chromatography (methylene chloride/methanol, 98/2) afforded 0.61 g (61%) of product. The free base (0.5 g, 1.31 mmol) was dissolved in ethanol, and precipitated with one equivalent of oxalic acid in ethanol to give the title compound (0.47 g, 76%) as the monooxalate, 0.25 hydrate: mp 91° C.; $^1$H NMR (DMSO, 400 MHz), 1.44–1.47 (m, 2H), 1.78–1.81 (m, 3H), 2.62 (d, 2H), 2.88–2.95 (m, 2H), 3.34–3.40 (m, 4H), 3.46–3.49 (m, 2H), 3.74 (s, 3H), 4.25 (t, 2H), 6.86–7.33 (m, 8H), 10.97 (br s, 1H); MS (EI) m/z 382 (M$^+$).

Elemental Analysis Calcd for $C_{23}H_{27}FN_2O_2 \cdot C_2H_2O_4 \cdot 0.25H_2O$ Theory: C, 62.95; H, 6.23; N, 5.87. Found: C, 63.00; H, 6.60; N, 5.47.

EXAMPLE 2

5-Fluoro-3-{1-[2-(2,3-dihydrobenzo[1,4]dioxin-5-yloxy)ethyl]-piperidin-4-ylmethyl}-1H-indole.

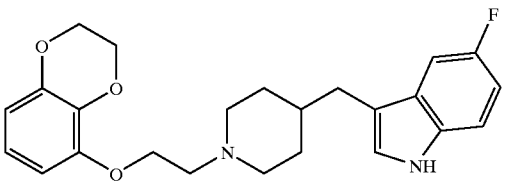

To a solution of 5-fluoro-3-[(4-piperidinyl)methyl]-1H-indole (0.35 g, 1.5 mmol) in DMSO (10 mL) was added 5-(2-chloroethoxy)-(2,3)-dihydrobenzo[1,4]dioxan (0.32 g, 1.5 mmol) followed by addition of triethylamine (0.42 mL, 3.0 mmol) at room temperature. The reaction mixture was heated to 80° C. for 3 h and cooled. The reaction was quenched with water, diluted with methylene chloride. The two layers were separated and the aqueous was extracted with methylene chloride. The combined organic extracts were washed with water, dried over anhydrous sodium sulfate, filtered and concentrated. Purification by silica gel column chromatography (ethyl acetate/methanol/ammonia, 99/1/0.1) afforded 0.36 g (58%) of a solid. The free base (0.33 g, 0.80 mmol) was dissolved in 2-propanol, and precipitated with one equivalent of fumaric acid in 2-propanol to give the title compound (0.35 g, 83%) as monofumarate, 0.5 hydrate: mp 157–159° C.; $^1$H NMR (DMSO, 400 MHz), 1.25–1.31 (m, 2H), 1.58–1.65 (m, 3H), 2.19–2.25 (m, 2H), 2.56–2.58 (m, 2H), 2.81–2.84 (m, 2H). 3.04–3.06 (m, 2H), 4.06 (t, 2H), 4.18 (s, 4H), 6.44–7.32 (m, 7H), 10.89 (br s, 1H); MS (EI) m/z 410 (M$^+$).

Elemental Analysis Calcd. for $C_{24}H_{27}FN_2O_3 \cdot C_4H_4O_4 \cdot 0.5H_2O$ Theory: C, 62.79; H, 6.02; N, 5.23. Found: C, 62.61; H, 5.98.; N, 4.88.

EXAMPLE 3

5-Fluoro-3-{1-[2-(indan-5-yloxy)-ethyl]-piperidin-4-ylmethyl}-1H-indole

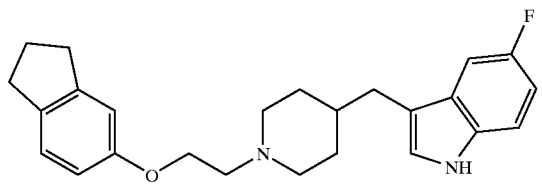

To a solution of 5-fluoro-3-[(4-piperidinyl)methyl]-1H-indole (0.35 g, 1.5 mmol) in DMSO (10 mL) was added 5-(2-chloroethoxy)indane (0.30 g, 1.5 mmol) followed by addition of triethylamine (0.42 mL, 3.0 mmol) at room temperature. The reaction mixture was heated to 80° C. for 3 h and cooled. The reaction was quenched with water, diluted with methylene chloride. The two layers were separated and the aqueous was extracted with methylene chloride. The combined organic extracts were washed with water, dried over anhydrous sodium sulfate, filtered and concentrated. Purification by silica gel column (ethyl acetate/methanol/ammonia hydroxide, 99/1/0.1) afforded 0.28 g (48%) of a solid. The free base (0.25 g, 0.63 mmol) was dissolved in ethyl acetate, and precipitated with one equivalent of HCl in ether to give the title compound (0.19 g, 45%) as monohydrochloride, 0.25 hydrate: mp 150–152° C.; $^1$H NMR (DMSO, 400 MHz), 1.48–1.57 (m, 2H), 1.78–1.81 (m, 3H), 1.95–2.02 (m, 2H), 2.59–2.61 (m, 2H), 2.74–2.82 (m, 4H), 2.91–2.99 (m, 2H), 3.37–3.57 (m, 4H), 4.31 (t, 2H), 6.69–7.33 (m, 7H), 10.23 (br s, 1H), 11.98 (br s, 1H); MS (EI) m/z 392 (M$^+$).

Elemental Analysis Calcd for $C_{25}H_{29}FN_2O \cdot HCl \cdot 0.25H_2O$ Theory: C, 69.27; H, 7.09; N, 6.46. Found: C, 69.32; H, 7.08.; N, 6.32.

EXAMPLE 4

3-{1-[2-(2,3-Dihydro-benzo[1,4]dioxan-5-yloxy)-ethyl]-1,2,3,6-tetrahydro-pyridin-4-yl}-1H-indole

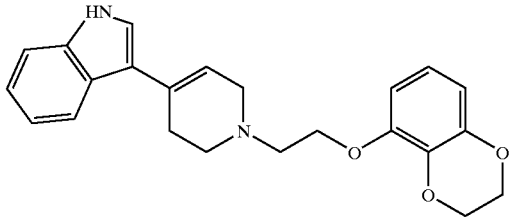

To a solution of 5-(2-chloroethoxy)-(2,3)-dihydrobenzo[1,4]dioxan (500 mg, 2.33 mmol), 1,2,3,6-tetrahydropyridin-4-yl-1H-indole (462 mg, 2.33 mmol) and triethylamine (0.645 mL, 4.66 mmol) in DMSO (20 mL) was stirred at 80° C. overnight. The reaction mixture was cooled, quenched with H$_2$O and diluted with EtOAc. The organic layer was washed with 3×100 mL H$_2$O, dried over Na$_2$SO$_4$, and concentrated. Purification by column chromatography (5% MeOH/CH$_2$Cl$_2$) afforded 150 mg (17%) of the title compound as a gold oil. The oxalate salt was formed by dissolving the free base in THF (20 mL) and adding oxalic acid dissolved in THF: mp 85–88° C.; $^1$H NMR (DMSO) δ7 2.8 (2H, br, m), 3.46 (4H, br, m), 3.89 (2H, br, m), 4.25 (4H, m), 4.33 (2H, t), 6.17 (1H, s), 6.54 (1H, dd), 6.65 (1H, dd), 6.76 (1H, t), 7.04–7.16 (2H, m), 7.41 (1 H, d), 7.52 (1 H, d), 11.29 (1 H, s); MS (EI) m/z 376 (M$^+$).

Elemental Analysis Calcd. For $C_{23}H_{24}N_2O_4 \cdot C_2H_2O_4 \cdot 0.80H_2O$ Theory: C, 62.44; H, 5.79; N, 5.82 Found: C, 62.59; H, 5.86; N, 5.42

EXAMPLE 5

5-Fluoro-3-{1-[2-(2,3-dihydro-benzo[1,4]dioxan-5-yloxy)-ethyl]-1,2,3,6-tetrahydro-pyridin-4-yl}-1H-indole

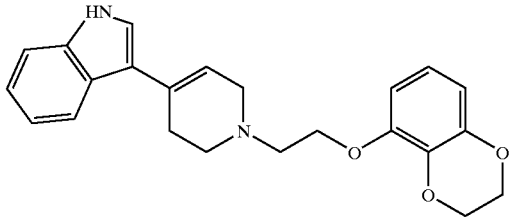

Replacing 1,2,3,6-tetrahydropyridin-4-yl-1H-indole with 5-fluoro-3-[1,2,3,6-tetrahydro-pyridin-4-yl]-1H-indole (444 mg, 2.05 mmol) in the procedure for Example 4 afforded the title compound 280 mg (61%) as a light green oil. The oxalate salt was prepared in EtOH to afford a yellow solid: mp 195–198° C; $^1$H NMR (DMSO) δ2.78 (2H, br, s), 3.45 (4H, m), 8.88 (2H, br, s), 4.26 (4H, m), 4.32 (2H, t), 6.11 (1 H, s), 6.53 (1 H, dd), 6.63 (1H, dd), 6.75 (1H, t), 7.4 (1H, dd), 7.50–7.57 (2H, m), 11.41 (I H, s); MS (APCI) m/z 395 [M+H]$^+$.

Elemental Analysis Calcd. For $C_{23}H_{23}FN_2O_4 \cdot C_2H_2O_4$ Theory: C, 61.94; H, 5.20; N, 5.78 Found: C, 61.59; H, 5.15; N, 5.94

EXAMPLE 6

6-Fluoro-3-{1-[2-(2,3-dihydro-benzo[1,4]dioxan-5-yloxy)-ethyl]-1,2,3,6-tetrahydro-pyridin-4-yl}-1H-indole

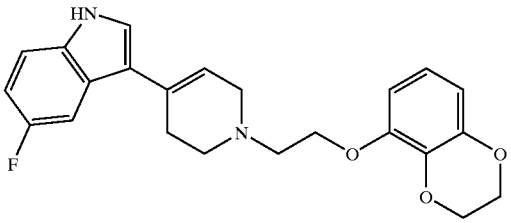

Replacing 1,2,3,6-tetrahydropyridin-4-yl-1H-indole with 6-F-3-[1,2,3,6-tetrahydropyridin-4-yl]-1H-indole (328 mg, 1.51 mmol) in the procedure for Example 4 afforded the title compound 230 mg (50%) as a viscous gold oil. The oxalate salt was prepared by adding the free base and oxalic acid in EtOH and heating to dissolve. Upon cooling to rt. crystals of the oxalate salt formed: mp 201–202° C.; $^1$H NMR (DMSO) δ2.75 (2H, br, s), 3.44 (4H, br, s), 3.86 (2H, br, s), 4.24 (4H, m), 4.31 (2H, t), 6.15 (1H, s), 6.52 (1H, dd), 6.63 (1H, dd), 6.75 (1H, t), 6.88–6.94 (1H, m), 7.17 (1H, dd)7.50 (1H, d), 8.80–7.84 (1H, m), 11.06 (1H, s); MS (APCI) m/z 395 [M+H]$^+$.

Elemental Analysis Calcd. For $C_{23}H_{23}FN_2O_4 \cdot C_2H_2O_4$
Theory: C, 61.94; H, 5.20; N, 5.78 Found: C, 61.41; H, 5.19; N, 5.94

The results of the tests with compounds representative of this invention are given in the immediately following table.

| Example No. | Ki (nM) Serotonin Transporter [3H]paroxetine | Ki (nM) 5-HT1A [3H]DPAT |
|---|---|---|
| 1 | 0.35 | 180 |
| 2 | 0.011 | 168 |
| 3 | 2.24 | 0% @ 0.1 M |
| 4 | 0.17 | 78.26 |
| 5 | 1.17 | 83.30 |
| 6 | 0.15 | 83.65 |

The compounds of this invention are useful in methods for the treatment of depression as well as other serotonin-related disorders including, but not limited to, anxiety, generalized anxiety disorder, panic disorder, obsessive-compulsive disorder, sleep disorders, sexual dysfunction, bipolar disorders, psychosis, stress-related disorders, including post-traumatic stress disorders, Tourettes' syndrome, attention deficit disorder, with and without hyperactivity, alcohol and drug addiction, Alzheimer's disease, Parkinson's disease, obesity and acute and chronic pain, including migraine pain. Chemical dependencies and addictions which may be treated with compounds of this invention include those to opiates, benzodiazepines, cocaine, nicotine and ethanol.

The compounds herein are also useful in methods of enhancing cognition in a mammal, preferably a human, particularly in a mammal experiencing a cognitive deficit as a result of or in association with Alzheimer's disease or Parkinson's disease.

Each of these methods of treatment comprise administering a pharmaceutically effective amount of a compound of this invention, or a pharmaceutically acceptable salt thereof, to a mammal in need of such treatment or enhancement. A pharmaceutically or therapeutically effective amount of the compounds herein is understood to comprise an amount of the compound(s) in question which will obtain at least a minimum of desired effect in preventing, treating, inhibiting or managing the symptoms or causes of the malady in question. More preferably, the amount will be the minimum needed to alleviate or remove the undesirable physiological consequences of the malady in question and inhibit or prevent their re-occurrence.

This invention also provides pharmaceutical formulations comprising a pharmaceutically or therapeutically effective amount of a compound of this invention, or a pharmaceutically acceptable salt thereof, and a pharmaceutically acceptable carrier or excipient.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

What is claimed:

1. A compound of the formula:

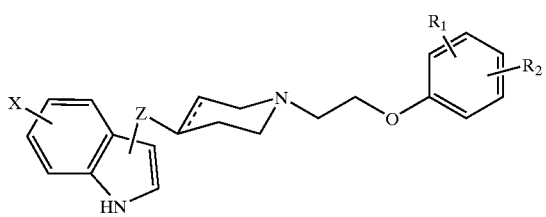

I wherein:

$R_1$ and $R_2$ are adjacent to each other and concatenated to form another ring wherein the ring is not aryl and contains a total of 5–7 ring members consisting of carbon atoms and up to two oxygen atoms;

X is selected from hydrogen, halogen, cyano, or $C_1$–$C_6$ alkoxy;

Z is $(CH_2)_n$ or carbonyl;

n is 0, 1 or 2;

the dashed line indicates an optional double bond;

or a pharmaceutically acceptable salt thereof.

2. A compound of claim 1, or a pharmaceutically acceptable salt thereof, wherein the moiety:

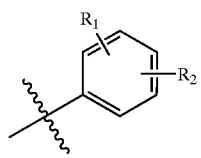

represents a moiety selected from the group of:

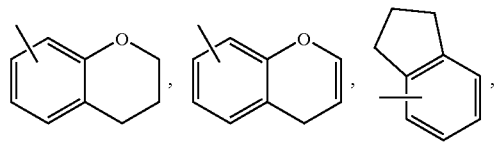

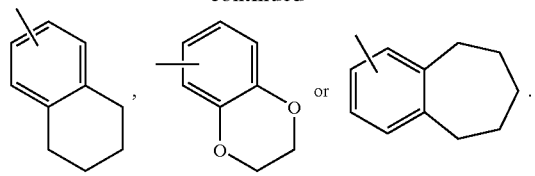

3. A compound of claim 1 of the formula:

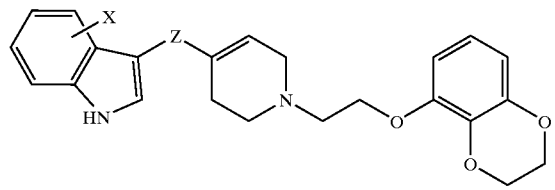

wherein X is selected from H, halogen, cyano, $C_1$–$C_6$ alkoxy; Z is $(CH_2)n$ or carbonyl;

and n is 0, 1 or 2; or a pharmaceutically acceptable salt thereof.

4. A compound of claim 1 of the formula:

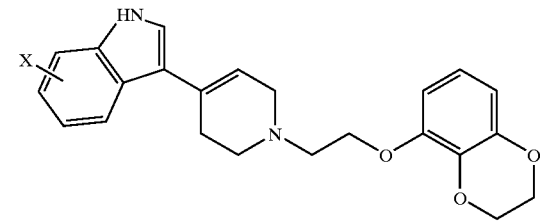

wherein X is H, halogen, cyano, $C_1$–$C_6$ alkoxy, or a pharmaceutically acceptable salt thereof.

5. A compound of claim 1 of the formula:

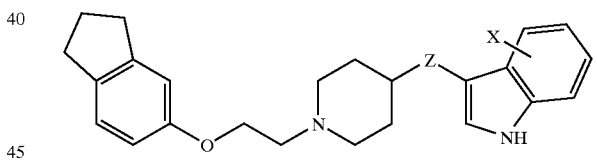

wherein X is selected from H, halogen, cyano, $C_1$–$C_6$ alkoxy; Z is $(CH_2)n$ or carbonyl;

and n is 0, 1 or 2; or a pharmaceutically acceptable salt thereof.

6. A compound of claim 1 wherein the pharmaceutically acceptable salt form thereof is selected from those formed as an addition salt form from fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric or nitric acid.

7. A compound which is 5-Fluoro-3-{1-[2-(2-methoxyphenoxy)ethyl]-piperidin-4-ylmethyl}-1H-indole, or a pharmaceutically acceptable salt thereof.

8. A compound of claim 1 which is 5-Fluoro-3-{1-[2-(2,3-dihydrobenzo[1,4]dioxin-5-yloxy)ethyl]-piperidin-4-ylmethyl}-1H-indole, or a pharmaceutically acceptable salt thereof.

9. A compound of claim 1 which is 5-Fluoro-3-{1-[2-(indan-5-yloxy)-ethyl]-piperidin-4-ylmethyl}-1H-indole, or a pharmaceutically acceptable salt thereof.

10. A compound of claim 1 which is 3-{1-[2-(2,3-Dihydro-benzo[1,4]dioxan-5-yloxy)-ethyl]-1,2,3,6-tetrahydro-pyridin-4-yl}-1H-indole, or a pharmaceutically acceptable salt thereof.

11. A compound of claim 1 which is 5-Fluoro-3-{1-[2-(2,3-dihydro-benzo[1,4]dioxan-5-yloxy)-ethyl]-1,2,3,6-tetrahydro-pyridin-4-yl}-1H-indole, or a pharmaceutically acceptable salt thereof.

12. A compound of claim 1 which is 6-Fluoro-3-{1-[2-(2,3-dihydro-benzo[1,4]dioxan-5-yloxy)-ethyl]-1,2,3,6-tetrahydro-pyridin-4-yl}-1H-indole, or a pharmaceutically acceptable salt thereof.

13. A pharmaceutical composition comprising a pharmaceutically effective amount of a compound of claim 1, or a pharmaceutically acceptable salt thereof, and a pharmaceutically acceptable carrier or excipient.

14. A method of treating depression in a mammal, the method comprising administering to a mammal in need thereof a pharmaceutically effective amount of a compound of claim 1, or a pharmaceutically acceptable salt thereof.

15. A method of treating anxiety in a mammal, the method comprising administering to a mammal in need thereof a pharmaceutically effective amount of a compound of claim 1, or a pharmaceutically acceptable salt thereof.

* * * * *